United States Patent [19]

Lamont

[11] Patent Number: 4,478,214
[45] Date of Patent: Oct. 23, 1984

[54] MEDICAL BOOT APPARATUS, AND METHODS OF CONSTRUCTING AND UTILIZING SAME

[76] Inventor: William D. Lamont, 24609 Spring La., Mt. Clemens, Mich. 48043

[21] Appl. No.: 477,498

[22] Filed: Mar. 21, 1983

[51] Int. Cl.³ ............................................. A61B 19/00
[52] U.S. Cl. ..................................... 128/149; 128/153
[58] Field of Search ............... 128/149, 153, DIG. 20, 128/80 R, 80 H, 82, 89 R; 36/4, 9, 93

[56] References Cited

U.S. PATENT DOCUMENTS

| | | | |
|---|---|---|---|
| 2,911,657 | 11/1959 | Streeter | 128/149 X |
| 3,606,884 | 9/1971 | Peter | 128/149 X |
| 4,076,022 | 2/1978 | Walker | 128/149 |
| 4,369,588 | 1/1983 | Berguer | 36/9 R |

*Primary Examiner*—John D. Yasko
*Attorney, Agent, or Firm*—Irving M. Weiner; Pamela S. Burt; Anthony L. Cupoli

[57] ABSTRACT

A medical boot apparatus for use during treatment and healing of a vascular or other foot disorder. The apparatus includes a main body portion having an upper front opening and open toe portion, and a sole portion formed with a forward rim for protecting the toes. A raised heel cord portion is formed along an inner rear surface of the main body portion so as to support the back of a bedridden patient's leg such that the heel is elevated with no pressure exerted thereagainst. At least one fluid cushioning member is provided at the raised heel cord portion so as to cushion the back leg portion of the patient. The boot includes particular features designed to protect the foot under both bedridden and ambulatory conditions, and affords protection from trauma, abrasions, decubitus ulcer formation, moisture accumulation, external pressures, heat loss, etc.

15 Claims, 5 Drawing Figures

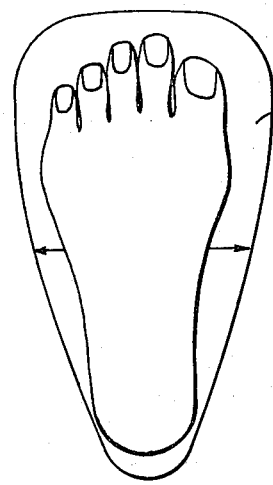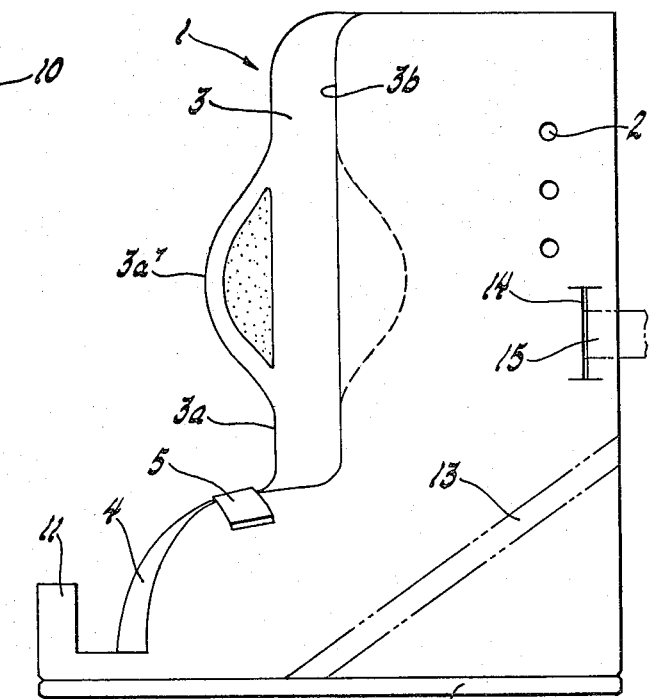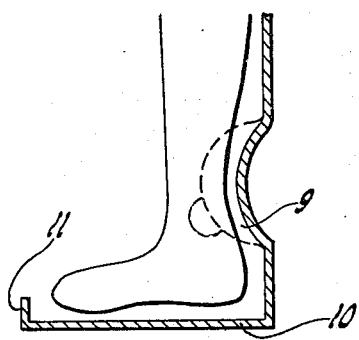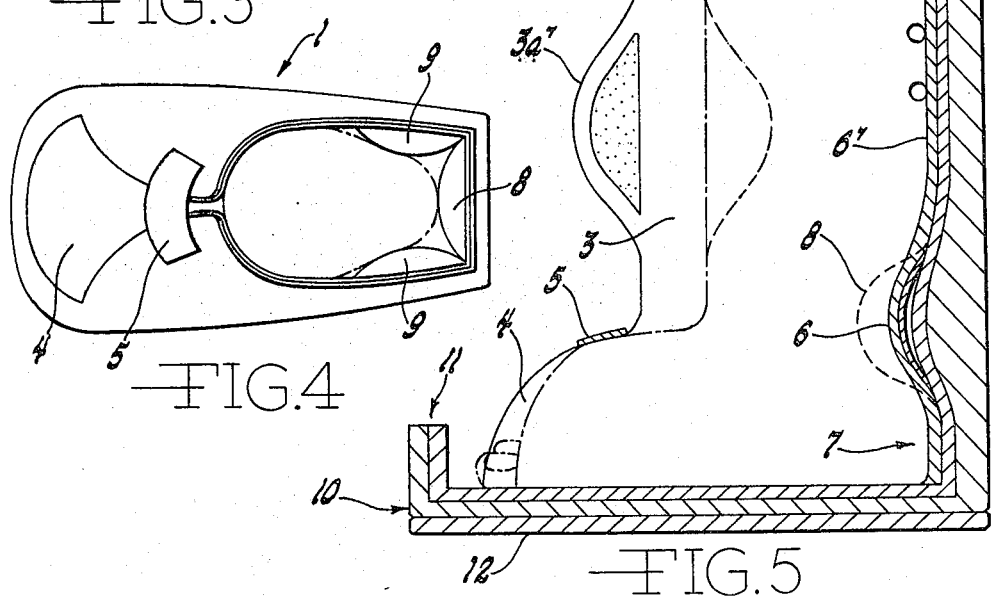

MEDICAL BOOT APPARATUS, AND METHODS OF CONSTRUCTING AND UTILIZING SAME

BACKGROUND OF THE INVENTION

1. Field of the Invention

The present invention relates generally to a medical boot apparatus for use in protecting the foot of a supine or bedridden patient. More particularly, the invention relates to a medical boot apparatus which is especially useful during treatment and healing of a vascular patient or other type of bedridden patient so as to protect the patient's foot from trauma, decubitus ulcer formation, undesirable moisture accumulation, external pressures from the bed and bedsheets, heat loss, etc.

2. Description of Relevant Art

In the treatment of patients with vascular problems, particularly when the patient is supine or bedridden following vascular surgery, a number of particular problems arise which are likely to interfere with the healing process and moreover to subject the patient to considerable pain. In particular, during treatment and healing of a vascular disorder which affects the patient's extremities, it is critical that the affected extremity be protected from trauma and external pressures.

When the vascular problem affects the patient's foot, for example, it is desirable that the foot be held in a position so as to prevent pressure on the heel, which would normally result when the heel rests against the bed surface for protracted bedridden periods and which exposes the patient to possible formation of decubitus ulceration of the heel. One known technique for preventing such pressure on the patient's heel involves the use of a heel cup which is positioned between the bed surface and the patient's heel. However, the heel cup is undesirable from the standpoint that the weight of the extremity will be supported over a relatively small area (i.e., at only the periphery of the cup).

A number of other significant problems associated with the treatment and healing of the foot also arise, and are not overcome by the aforesaid heel cup. Undesirable pressure is also exerted on the affected foot from above by the bedsheets resting on the patient's toes. Moreover, peripheral vascular diseases such as gangrene, ischaemia, edematous, venous stasis and other painful and destructive conditions are likely to arise in the affected area. The patient is also likely to experience severe coldness and even numbness in the affected foot due to insufficient blood circulation.

With the foregoing serious problems in mind, it is also important that any apparatus provided for protecting the patient's foot afford sufficient air circulation around the foot, and permit access to the foot for performing pulse checks, inspection and dressing changes, if necessary.

A known apparatus designed to overcome the foregoing problems is the "Vascular Boot" by Lunax Corporation (distributed by LaMed Inc. of Pleasant Ridge, Mich.). Such boot is fabricated of a lightweight open cell foam material with non-woven polyester interior and exterior surfaces. The boot has a split-front opening with Velcro strap fasteners, a closed toe portion, and a solid sole. A heel cord lift is formed by a calf and heel insert disposed within the boot so as to support the weight of the extremity over the lower third of the leg and thereby prevent pressure on the heel.

However, the aforesaid "Vascular Boot" has several attendant disadvantages. For example, the boot has a substantially closed construction, which is undesirable with respect to air circulation and ready visual inspection. Further, although the heel is protected from pressure by means of the calf and heel insert, the insert itself can cause discomfort and possible peripheral vascular problems in the leg area supported thereby.

The present invention provides an improved medical boot apparatus which overcomes the problems attendant known devices, and at the same time meets all of the aforesaid desirable requirements of a protection apparatus for the patient'foot.

SUMMARY OF THE INVENTION

The present invention provides a medical boot apparatus comprising a substantially boot-shaped main body portion fabricated of a substantially flexible shape-retentive material, the main body portion having an upper front opening extending downwardly to a substantially open toe portion. The sole portion of the main body portion includes a forwardmost portion extending beyond the open toe portion, and means are provided for selectively fastening the upper front opening in a closed position. A raised heel cord portion is formed along an inner rear surface of the main body portion so as to support the back of a bedridden patient's leg when it is positioned in the main body portion, such that the patient's heel is elevated with no pressure exerted thereagainst. First fluid cushioning means is provided on the raised heel cord portion for cushioning the back leg portion of the patient supported by the raised heel cord portion.

In a preferred embodiment of the invention, the first fluid cushioning means comprises a substantially flexible water or air impervious cushion member having water or air sealed therein, the cushion member being secured to the raised heel cord portion so as to be disposed between such raised portion and the back of the patient's leg.

Desirably, second fluid cushioning means are provided on each respective side of the first fluid cushioning means.

It is an object of the present invention to provide a medical boot apparatus wherein the patient's heel is supported in an elevated position with no pressure exerted thereagainst, by means of the raised heel cord portion which itself is provided with fluid cushioning means to ensure comfort and protection for the back of the patient's leg supported by the raised heel cord portion.

Another object of the present invention is to provide a medical boot apparatus which permits efficient air circulation for the patient's foot received therein.

Still a further object of the invention is to provide means for immobilizing the patient's foot so as to particularly prevent the development of a drop-foot or flacid foot condition.

The above and further objects, details and advantages of the present invention will become apparent from the following detailed description, when read in conjunction with the accompanying drawings.

BRIEF DESCRIPTION OF THE DRAWINGS

FIG. 1 is a cut-away top view of the sole portion of the medical boot apparatus according to the invention, with a patient's foot positioned thereon.

FIG. 2 is a side elevational view of a medical boot apparatus in accordance with an embodiment of the present invention.

FIG. 3 is a sectioned side view of a medical boot apparatus according to the invention, showing a patient's foot positioned therein.

FIG. 4 is a top plan view of the medical boot apparatus shown in FIG. 2.

FIG. 5 is a sectioned side view of the medical boot apparatus according to the invention.

DETAILED DESCRIPTION OF PREFERRED EMBODIMENTS

With reference to FIGS. 2–5, the medical boot apparatus in accordance with the invention comprises a main body portion 1 fabricated of a substantially flexible shape-retentive material, such as polyurethane foam rubber. Such material is specifically adapted to afford air penetration to the patient's foot, while at the same time minimizing undesirable heat loss. Also, the material is soft and pliant to avoid irritation of the patient's skin. Additional air ventilation is afforded by means of a plurality of air vent holes 2, which may be provided in any desired number and configuration.

The main body 1 is provided with an upper front opening 3 extending downwardly to a substantially open toe portion 4 so as to be integrally open therewith. The upper front opening 3 is defined by two open side edges 3a and 3b of the main body 1. The side edge 3a is provided with an integral extended contoured portion 3a' which is adapted to be wrapped in overlapping relation over the opposite side edge 3b as shown in broken line in FIGS. 2 and 5. If desired, the inner surface of contoured extension 3a may be provided with a fastener such as a Velcro fastener.

In operation, once the patient's foot has been positioned within the main body 1, the side edge 3a' (by means of contoured extension 3a') is wrapped around the patient's leg so as to be in overlapping relation to the opposite side edge 3b. Varying leg sizes can thus be readily accommodated by the extent of overlap of the side edge 3a relative to the side edge 3b.

The open toe portion 4, as shown most clearly in FIG. 4, provides for substantial open exposure of the entire toe area of the patient's foot. Such open construction serves to enhance air ventilation to the patient's foot, and particularly the toe area wherein moisture problems are otherwise likely to develop, thus greatly reducing the likelihood of peripheral vascular disease such as gangrene. Ready visual inspection of and access to the toe area is also enhanced by the open toe construction. A Velcro fastener 5 operatively cooperates with the respective open side edges of the main body 1 adjacent the open toe portion 4 so as to permit selective fastening closure of the front of the boot.

The inner rear surface of main body 1 is provided with a raised heel cord portion 6. The raised portion 6 may be defined in a relatively rigid liner 6' (FIG. 5), formed of plastic for example, extending along at least the rear inner portion of main body 1; or may alternatively be formed of a bulk of material, such as foam rubber. When the patient is lying in a supine position, the weight of the extremity will be supported by the back of the patient's leg at the heel cord portion by means of raised portion 6 of the boot. In this position, the patient's heel will be supported in a somewhat elevated position such that no pressure is exerted thereagainst, i.e., it will be elevated above the heel portion 7 (FIG. 5) of the boot. By thus relieving pressure off the patient's heel, substantial discomfort and peripheral vascular diseases such as decubitus ulcer are substantially prevented from occurring.

A substantially flexible cushion member 8 is secured, such as by adhesion, to the raised portion 6 so as to be disposed between raised portion 6 and the patient's leg. The flexible cushion member 8 may preferably be formed of a vinyl material which is water and air impervious. The cushion member 8 is filled with a fluid, such as either water or air, which is sealed therein. When the patient is positioned in the aforesaid supine position with the boot received over the foot, the cushion member 8 will effectively cushion the back of the patient's leg in the heel cord area (which supports the weight of the extremity), thus greatly enhancing patient comfort while reducing irritation to the supported leg area. A pair of side cushion members 9 (FIGS. 3 and 4) are also provided, and have substantially the same construction as cushion member 8. The side cushion members 9 are disposed respectively on either side of the cushion member 8 so as to support and cushion the sides of the patient's leg and the ankles, and may be adhesively or otherwise secured in position.

With the foregoing arrangement of cushion members 8 and 9, the rear of the patient's foot will be comfortably cushioned and wedged in a stationary position as shown in FIG. 4. As shown in FIGS. 1 and 4, the sole portion 10 of the boot is configured such that the width thereof gradually increases from the rear heel portion to the front toe portion thereof. The width of the sole portion thus provides sufficient space around the foot to permit dressings to be received therein, while the expanded sole area at the toe portion permits toe flexing if desired.

The sole portion 10 of the main body 1 extends forwardly beyond the open toe portion 4 and is bent upwardly to define a forwardmost rim or flange 11. Desirably, a relatively rigid liner portion (FIG. 5) may coextend with sole portion 10 to enhance the rigidity thereof. The forwardmost flange 11 of sole portion 10 defines a protective rim which protects the toes from trauma and protects the foot from the pressure of bed linens from above when the patient is in a bedridden state.

The lower surface of sole portion 10 is provided with a coextensive gripping sole portion 12 which is integrally fixed to sole portion 10. The gripping sole portion 12 provides a friction surface which permits the patient to ambulate without the fear of slipping or losing his footing.

As shown in dashed line in FIG. 2, the main body 1 may have secured thereto a diagonal support strip 13 made of plastic, for example. The support strip 13 is diagonally secured between the sole portion 12 and the rear leg portion of the main body 1 so as to ensure substantially a right-angle support of sole portion 12 relative to the remainder of the boot. Such right-angle support of sole portion 12 substantially prevents the patient's foot from flexing downwardly, thus preventing development of a drop-foot or flacid foot condition which otherwise might develop as the patient's heel cord begins to shorten under bedridden conditions.

As another feature, the medical boot apparatus in accordance with the invention may desirably be provided with an anti-rotation means which prevents rotation of the patient's foot within main body 1. As shown in FIG. 2, such anti-rotation means comprises a slit-like opening 14 formed in main body portion 1 above the raised portion 6. A substantially flat elongated rigid bar 15 formed of plastic or the like is adapted to be received within slit 14. When the thus-inserted bar 15 is brought to bear against the patient's leg, undesirable rotation of the leg within the boot may be effectively prevented. By way of example, the bar 15 may have dimensions of approximately 2×6×¼ inches.

The medical boot apparatus according to the present invention, constructed as described hereinabove, provides a number of advantageous features, as will be understood from the foregoing. The boot effectively protects the patient's foot and lower leg from trauma, and minimizes any possibility of heel and ankle bone decubitus ulcer formation in a bedridden patient. The boot is configured and dimensioned to facilitate accessibility to the foot and leg for inspection, pulse checks, dressing changes and the like, and at the same time ensures proper air ventilation so as to minimize any possibility of gangrene or other peripheral vascular diseases developing. The boot is also useful to the ambulatory patient in that the foot is protected from abrasions or injuries during ambulation, while the gripping sole portion prevents slipping.

Although the medical boot apparatus in accordance with the invention is particularly useful for the treatment and healing of vascular patients, it is not limited to such use. Neurology patients, physical therapy patients, burn patients, surgical patients and emergency room trauma patients are also amongst the many types of patients that can benefit from the advantageous features afforded by the present invention.

Further, although there have been described what are at present considered to be the preferred embodiments of the invention, it will be understood that various modifications may be made therein without departing from the spirit or essential characteristics thereof. The present embodiments are therefore to be considered in all respects as illustrative, and not restrictive. The scope of the invention is indicated by the appended claims rather than by the foregoing description.

I claim:

1. A medical boot apparatus, comprising:
   a substantially boot-shaped main body portion fabricated of a substantially flexible shape-retentive material;
   said main body portion having an upper front opening extending downwardly to a substantially open toe portion;
   the sole portion of said main body portion including a forwardmost portion extending beyond said open toe portion;
   means for selectively fastening said upper front opening in a closed position;
   a raised heel cord portion formed along an inner rear surface of said main body portion so as to support the back of a bedridden patient's leg when it is positioned in said main body portion such that the patient's heel is elevated with no pressure exerted thereagainst; and
   first fluid cushioning means provided on said raised heel cord portion for cushioning the back leg portion of said patient supported by said raised heel cord portion.

2. A medical boot apparatus according to claim 1, wherein:
   said main body portion is provided with a relatively rigid liner extending along at least the rear portion of said main body portion; and
   said raised heel cord portion is formed along an inner rear surface of said relatively rigid liner.

3. A medical boot apparatus according to claim 1, wherein:
   a gripping sole portion is integrally fixed to said sole of said main body portion so as to provide a gripping sole surface for an ambulating patient.

4. A medical boot apparatus according to claim 1, wherein: said main body portion is provided with a plurality of air vent holes.

5. A medical boot apparatus according to claim 1, wherein:
   said first fluid cushioning means comprises a substantially flexible and water impervious cushion member having water sealed therein; and
   said cushion member is secured to said raised heel cord portion so as to be disposed between said raised portion and the back of the patient's leg when the patient's foot is received in said main body portion.

6. A medical boot apparatus according to claim 1, wherein:
   said first fluid cushioning means comprises a substantially flexible and air impervious cushion member having air sealed therein; and
   said cushion member is secured to said raised heel cord portion so as to be disposed between said raised portion and the back of the patient's leg when the patient's foot is received in said main body portion.

7. A medical boot apparatus according to claim 1, wherein:
   second fluid cushioning means are provided on each respective side of said first fluid cushioning means.

8. A medical boot apparatus according to claim 6, wherein:
   said second fluid cushioning means comprises a pair of substantially flexible and water impervious cushion members having water sealed therein; and
   said pair of cushion members are respectively secured at respective sides of said raised portion so as to be disposed between said main body portion and the sides of the patient's leg when the patient's foot is received in said main body portion.

9. A medical boot apparatus according to claim 6, wherein:
   said second fluid cushioning means comprises a pair of substantially flexible and air impervious cushion members having air sealed therein; and
   said pair of cushion members are respectively secured at respective sides of said raised portion so as to be disposed between said main body portion and the sides of the patient's leg when the patient's foot is received in said main body portion.

10. A medical boot apparatus according to claim 1, wherein:
    said upper front opening of said main body portion includes two open side edges of said main body portion; and
    one of said open side edges comprising an extended contoured wrap portion adapted to be wrapped in overlapping relation over the other of said open side edges.

11. A medical boot apparatus according to claim 1, wherein:
    said fastening means comprises a Velcro fastener operatively cooperating with open side edges of said upper front opening so as to selectively close same.

12. A medical boot apparatus according to claim 1, wherein:
said main body portion is provided with a slit-like opening disposed above said raised heel cord portion; and
said apparatus further comprises a substantially flat elongated bar adapted to be received through said slit-like opening so as to prevent rotation of a patient's foot within said main body portion.

13. A medical boot apparatus according to claim 1, wherein:
a relatively rigid elongated member is diagonally secured between a rear portion of said main body member and said sole portion thereof so as to prevent downward flexing of said sole portion.

14. A medical boot apparatus according to claim 1, wherein:
said sole portion of said main body portion has a gradually increasing width from the rear heel portion thereof towards the front toe portion thereof.

15. A medical boot apparatus according to claim 1, wherein:
said forwardmost portion of said sole portion of said main body portion is provided with an upwardly-extending flange.

* * * * *